(12) United States Patent
Chen

(10) Patent No.: US 9,861,676 B2
(45) Date of Patent: Jan. 9, 2018

(54) HERBAL COMPOSITION AND METHOD OF USE

(71) Applicants: Wei-Ming Chen, Taipei (TW); Bo-Cheng Guo, Keelung (TW)

(72) Inventor: Wei-Ming Chen, Taipei (TW)

(73) Assignees: Wei-Ming Chen, Taipei (TW); Bo-Cheng Guo, Keelung (TW)

( * ) Notice: Subject to any disclaimer, the term of this patent is extended or adjusted under 35 U.S.C. 154(b) by 140 days.

(21) Appl. No.: 14/662,237

(22) Filed: Mar. 18, 2015

(65) Prior Publication Data

US 2016/0271201 A1   Sep. 22, 2016

(51) Int. Cl.
| | |
|---|---|
| *A61K 36/899* | (2006.01) |
| *A61K 36/28* | (2006.01) |
| *A61K 36/00* | (2006.01) |
| *A61K 36/8945* | (2006.01) |
| *A61K 36/344* | (2006.01) |
| *A61K 36/481* | (2006.01) |
| *A61K 36/8984* | (2006.01) |
| *A61K 36/8968* | (2006.01) |
| *A61K 36/488* | (2006.01) |
| *A61K 36/286* | (2006.01) |
| *A61K 36/48* | (2006.01) |
| *A61K 36/424* | (2006.01) |
| *A61K 36/62* | (2006.01) |
| *A61K 36/61* | (2006.01) |

(52) U.S. Cl.
CPC .......... *A61K 36/899* (2013.01); *A61K 36/286* (2013.01); *A61K 36/344* (2013.01); *A61K 36/424* (2013.01); *A61K 36/48* (2013.01); *A61K 36/481* (2013.01); *A61K 36/488* (2013.01); *A61K 36/61* (2013.01); *A61K 36/62* (2013.01); *A61K 36/8945* (2013.01); *A61K 36/8968* (2013.01); *A61K 36/8984* (2013.01)

(58) Field of Classification Search
None
See application file for complete search history.

(56) References Cited

U.S. PATENT DOCUMENTS

| | | | |
|---|---|---|---|
| 2002/0031559 A1* | 3/2002 | Liang | A61K 9/02 424/725 |
| 2004/0105902 A1* | 6/2004 | Chen | A61K 36/00 424/756 |
| 2009/0220667 A1* | 9/2009 | Johnson | A23F 5/14 426/595 |

* cited by examiner

*Primary Examiner* — Chris R Tate
*Assistant Examiner* — Russell Fiebig
(74) *Attorney, Agent, or Firm* — Cheng-Ju Chiang

(57) ABSTRACT

The present invention provides herbal compositions comprise Radix Dioscoreae, Radix Codonopsis, and Radix Astragalus Membranaceus. The herbal compositions are used to suppress intestinal glucose uptake of intestinal villus and decrease blood glucose levels. The present invention also provides methods of regulating blood glucose levels by administrating the herbal compositions.

7 Claims, No Drawings

HERBAL COMPOSITION AND METHOD OF USE

1. TECHNICAL FIELD

At least one embodiment of the present invention provides herbal compositions and methods of use for glycemic control. More particularly, at least one embodiment of the present invention provides herbal compositions and methods of use for glycemic control, in which the herbal compositions and methods of use are to suppress intestinal glucose uptake of intestinal villus and decrease blood glucose levels.

2. DESCRIPTION OF THE RELATED ART

Glucose is the primary source of energy for cells. The most typical route to uptake glucose is by transporting glucose from the intestines into the bloodstream, and the amount of glucose present in the blood is referred to as the blood glucose level. Glucose uptake and blood glucose level usually are tightly regulated by the body as a part of metabolic homeostasis. On the contrary, dysregulation of glucose uptake and blood glucose levels is usually correlated with medical conditions, such as hyperglycemia, hypoglycemia, ketoacidosis, seizure, Diabetes mellitus, and obesity.

Diabetes mellitus is a chronic disease which there is no known cure to permanently reverse the condition. People suffering from Diabetes mellitus are characterized by persistent hyperglycemia because of the defect in the insulin mechanism. The defects may be insufficient amount of insulin produced by the pancreas (Type 1 diabetes) or improper responses of the body to insulin (Type 2 diabetes). And the complications of Diabetes mellitus include cardiovascular disease, stroke, kidney failure, foot ulcers, damage to the eyes, and difficulty in wound healing.

The main goal of both glycemic management and diabetes manage is to restore carbohydrate metabolism to a normal state. Conventional approaches involving in the managements of carbohydrate metabolism are mostly focusing on insulin therapy and dietary programs. Insulin therapy provides external insulin or analogous proteins as a medication to promote the absorption of glucose from blood stream to skeletal muscles. Injection of insulin can rapidly remove excess glucose from the blood and thus adequately control blood glucose levels in body.

Another conventional approach to control blood glucose levels is the meal planning with low or medium glycemic index (GI) foods. GI is a number associated with a type of food that indicates the effect on raising the blood glucose levels. A food with a high GI raises blood glucose more than a food with a medium or low GI. And foods with low GIs tend to release glucose more gradually into the bloodstream, which usually equates to a lower insulin demand and may improve long-term blood glucose control and blood lipids.

However, insulin therapy and diet programs usually are not unsustainable in the long-term because of the feeling of inconvenience and deprivation. Insulin administration and dietary plans discourage participants by factors such as pain and inconvenience, and establish social barriers and rejections with a different life. Accordingly, there is a need for methods of controlling blood glucose levels with fewer disturbances in life.

SUMMARY

At least one embodiment of the present invention provides an herbal composition for glycemic control. The herbal composition comprises Radix Dioscoreae, Radix Codonopsis, and Radix Astragalus Membranaceus.

At least one embodiment of the present invention provides a method of regulating blood glucose levels, in which the method comprises an administering step to apply a therapeutically effective amount of the herbal composition to a subject. And the administering step is applied before a meal.

According to some embodiments, the herbal compositions further comprise pharmaceutically acceptable carrier and are formulated to be administered orally. The herbal compositions are applied to subjects to suppress intestinal glucose uptake of intestinal villus and therefore reduce the glycemic loads of foods. The inhibitory effect on glucose uptake may persist after stop taking the herbal compositions in some embodiments. The herbal compositions thus can be used to improve the quality of life of people suffering from poor glycemic control and people trying to reduce glucose uptake with ease, but without the feeling of deprivation from obtaining foods.

DESCRIPTION OF THE PREFERRED EMBODIMENTS

Some embodiments of the present invention provide herbal compositions for subjects having the need for glycemic control. The subjects may, for example, be people having one or more of the following conditions: hyperglycemia, Diabetes mellitus, and obesity. Some embodiments of the present invention also provide methods of regulating blood sugar levels.

In some embodiments, the herbal compositions comprise Radix Dioscoreae, Radix Codonopsis, and Radix Astragalus Membranaceus. In some other embodiments, the herbal compositions comprise Radix Dioscoreae, Radix Codonopsis, Radix Astragalus Membranaceus, Herba Dendrobii, Radix Ophiopogonis, and Radix Puerariae. In still some other embodiments, the herbal compositions comprises Radix Dioscoreae, Radix Codonopsis, Radix Astragalus Membranaceus, Herba Dendrobii, Radix Ophiopogonis, Radix Puerariae, Flos Carthami, Semen Dolichoris, Lophatherum gracile Brongn, Herba Gynostemmatis, Porphyra tenera, Semen Euryales, Psidium guajava leaf, Avena sativa, and bamboo cellulose.

Radix Dioscoreae is also named as "Radix Dioscoreae Oppositae" and "Shan Yao". Radix Dioscoreae is used to tonify spleen and stomach to improve appetite and energy and used as a remedy for chronic coughing and wheezing in traditional Chinese medicine. In some embodiments of the present invention, Radix Dioscoreae is prepared by processes including drying, grinding, and sifting. However, in some other embodiments, other conventional methods of herbal extraction may apply to Radix Dioscoreae.

Radix Codonopsis is also named as "Radix Codonopsitis Pilosulae" and "Dang Shen". Radix Codonopsis is used to increase the immunity of the body and used as an energy tonic acting mainly on spleen, stomach, and lungs in traditional Chinese medicine. In some embodiments of the present invention, Radix Codonopsis is prepared by processes including drying, grinding, and sifting. However, in some other embodiments, other conventional methods of herbal extraction may apply to Radix Codonopsis.

Radix Astragalus Membranaceus is also name as "Huang Qi". Radix Astragalus Membranaceus is used to tonify blood to increase the immune system of the body and used as a remedy for chronic fatigue, bruising, and bleeding in traditional Chinese medicine. In some embodiments of the present invention, Radix Astragalus Membranaceus is preserved in the form of alcohol herbal extracts. To use the alcohol herbal extract of Radix Astragalus Membranaceus in the embodiments, the alcohol herbal extracts are further processed by drying, grinding, and sifting. However, in some other embodiments, other conventional methods of herbal extraction may apply to Radix Astragalus Membranaceus.

Herba Dendrobii is also name as "Dendrobium Stem" and "Shi Hu". Herba Dendrobii is used to tonify kidney and eyes and as a remedy for chronic dry cough and dry mouth in traditional Chinese medicine. In some embodiments of the present invention, Herba Dendrobii is prepared by processes including drying, grinding, and sifting. However, in some other embodiments, other conventional methods of herbal extraction may apply to Herba Dendrobii.

Radix Ophiopogonis is also named as "Mai Dong", which is the root of Tuber Ophiopogonis Japonici. Radix Ophiopogonis is used to moisten the lungs, relieve dry tongue and thirst, and clear heat in the heart in traditional Chinese medicine. In some embodiments of the present invention, Radix Ophiopogonis is prepared by processes including drying, grinding, and sifting. However, in some other embodiments, other conventional methods of herbal extraction may apply to Radix Ophiopogonis.

Radix Puerariae is also named as "Ge Gen". Radix Puerariae is used to ease fever, relieve thirst, and stop diarrhea and dysentery in traditional Chinese medicine. In some embodiments of the present invention, Radix Ophiopogonis is prepared by processes including drying, grinding, and sifting. However, in some other embodiments, other conventional methods of herbal extraction may apply to Radix Ophiopogonis.

Flos Carthami is also known as "Flos Carthami Tinctorii" and "Hong Hua", which is the dry flower of Carthami Tinctorii. Flos Carthami is used as treatments for dysmenorrhea, postpartum pain, trauma, sports injuries, skin sores, carbuncles, measles, and paralysis in traditional Chinese medicine. In some embodiments of the present invention, Flos Carthami is prepared by processes including drying, grinding, and sifting. However, in some other embodiments, other conventional methods of herbal extraction may apply to Flos Carthami.

Semen Dolichoris is also named as "Semen Dolichoris Lablab" and "Bai Bian Dou". Semen Dolichoris is used to strengthen spleen to ease chronic diarrhea, vomiting, nausea, fatigue, and disinterest in food in traditional Chinese medicine. In some embodiments of the present invention, Semen Dolichoris is prepared by processes including drying, grinding, and sifting. However, in some other embodiments, other conventional methods of herbal extraction may apply to Semen Dolichoris.

Lophatherum gracile Brongn is also known as "Herba Lophatheri Gracilis" and "Dan Zhu Ye". Lophatherum gracile Brongn is used to reduce fever and promote urinary excretion and used as sedative to stabilize psychological functioning. In some embodiments of the present invention, Lophatherum gracile Brongn is preserved in the form of alcohol herbal extracts. To use the alcohol herbal extract of Lophatherum gracile Brongn in the embodiments, the alcohol herbal extracts are further processed by drying, grinding, and sifting. However, in some other embodiments, other conventional methods of herbal extraction may apply to Lophatherum gracile Brongn.

Herba Gynostemmatis is also named as "Herba Gynostemmatis Pentaphylli", "Rhizoma seu Herba Gynostemmatis", and "Jiao Gu Lan". Herba Gynostemmatis is used to mitigate inflammation, alleviate pain, and clear toxins in the body in traditional Chinese medicine. Herba Gynostemmatis is also believed to be beneficial to respiratory system and is able to moisten the lungs and remove phlegm in the throat. In some embodiments of the present invention, Herba Gynostemmatis is prepared by processes including drying, grinding, and sifting. However, in some other embodiments, other conventional methods of herbal extraction may apply to Herba Gynostemmatis.

Porphyra tenera is also known as "Nori" or "Zi Cai". Porphyra tenera is acting mainly on liver, lungs, and kidneys to relieve and dissipate phlegm and nodules in traditional Chinese medicine. Porphyra tenera is also known for the ability to promote urination. In some embodiments of the present invention, Porphyra tenera is prepared by processes including drying, grinding, and sifting. However, in some other embodiments, other conventional methods of herbal extraction may apply to Porphyra tenera.

Semen Euryales is also named as "gorgon seed" and "Qian Shi". Semen Euryales is acting mainly on spleen to stop chronic diarrhea and kidneys to prevent spermatorrhea in traditional Chinese medicine. In some embodiments of the present invention, Semen Euryales is prepared by processes including drying, grinding, and sifting. However, in some other embodiments, other conventional methods of herbal extraction may apply to Semen Euryales.

Psidium guajava leaf is used in some embodiments. The leaves of Psidium guajava are known for the anti-inflammation and analgesic properties in alternative medicine. Psidium guajava leaf is prepared by processes including drying, grinding, and sifting. However, in some other embodiments, other conventional methods of herbal extraction may apply to the leaves of Psidium guajava.

Avena sativa is also known as "oat". In traditional Chinese medicine, Avena sativa is able to boost fertility, improve sexual performance, promote energy, and strengthen the heart. Avena sativa also enhances digestion, reduces detoxification process and provides support for urinary organs in some folk remedies. In some embodiments of the present invention, Avena sativa is prepared by processes including drying, grinding, and sifting. However, in some other embodiments, other conventional methods of herbal extraction may apply to Avena sativa.

Bamboo cellulose is extracted or purified from natural bamboo plants. The bamboo cellulose contains plenty of cellulose and is prepared by processes including drying, grinding, and sifting in some embodiments of the present invention. However, in some other embodiments, other conventional methods of herbal extraction may apply to Bamboo cellulose.

In some embodiments, Radix Dioscoreae, Radix Codonopsis, Radix Astragalus Membranaceus, Herba Dendrobii, Radix Ophiopogonis, and Radix Puerariae are used to provide non-absorbable starches, in which the non-absorbable starches are mostly contained in Radix Dioscoreae, Radix Codonopsis, and Radix Astragalus Membranaceus. On the other hand, Flos Carthami, Semen Dolichoris, Lophatherum gracile Brongn, Herba Gynostemmatis, Porphyra tenera, Semen Euryales, Psidium guajava leaf, Avena sativa, and bamboo cellulose are used to provide cellulose.

In some embodiments, the herbal compositions comprise Radix Dioscoreae, Radix Codonopsis, and Radix Astragalus Membranaceus. In some certain embodiments, the herbal compositions comprise 1-50 wt % of Radix Dioscoreae, 1-50 wt % Radix Codonopsis, and 1-50 wt % of Radix Astragalus Membranaceus. In yet some certain embodiments, the herbal compositions comprise 10 wt % of Radix Dioscoreae, 10 wt % Radix Codonopsis, and 10 wt % of Radix Astragalus Membranaceus.

In some embodiments, the herbal compositions comprise Radix Dioscoreae, Radix Codonopsis, Radix Astragalus Membranaceus, Herba Dendrobii, Radix Ophiopogonis, and Radix Puerariae. In some certain embodiments, the herbal compositions comprise 1-30 wt % of Radix Dioscoreae, 1-30 wt % Radix Codonopsis, 1-30 wt % of Radix Astragalus Membranaceus, 1-10 wt % of Herba Dendrobii, 1-30 wt % of Radix Ophiopogonis, and less than 15 wt % of Radix Puerariae. In yet some certain embodiments, the herbal compositions comprise 10 wt % of Radix Dioscoreae, 10 wt % Radix Codonopsis, 10 wt % of Radix Astragalus Membranaceus, 3 wt % of Herba Dendrobii, 10 wt % of Radix Ophiopogonis, and less than 5 wt % of Radix Puerariae.

In some embodiments, the herbal compositions comprise Radix Dioscoreae, Radix Codonopsis, Radix Astragalus Membranaceus, Herba Dendrobii, Radix Ophiopogonis, Radix Puerariae, Flos Carthami, Semen Dolichoris, Lophatherum gracile Brongn, Herba Gynostemmatis, Porphyra tenera, Semen Euryales, Psidium guajava leaf, Avena sativa, and bamboo cellulose. In some certain embodiments, the herbal compositions comprise 1-20 wt % of Radix Dioscoreae, 1-20 wt % Radix Codonopsis, 1-20 wt % of Radix Astragalus Membranaceus, 1-6 wt % of Herba Dendrobii, 1-20 wt % of Radix Ophiopogonis, and less than 5 wt % of Radix Puerariae, 1-20 wt % of Flos Carthami, 1-20 wt % of Semen Dolichoris, 1-20 wt % of Lophatherum gracile Brongn, 1-10 wt % of Herba Gynostemmatis, 1-10 wt % of Porphyra tenera, 1-3 wt % of Semen Euryales, 1-20 wt % of Psidium guajava leaf, 1-20 wt % of Avena sativa, and 1-50 wt % of bamboo cellulose. In yet some certain embodiments, the herbal compositions comprise 10 wt % of Radix Dioscoreae, 10 wt % Radix Codonopsis, 10 wt % of Radix Astragalus Membranaceus, 3 wt % of Herba Dendrobii, 10 wt % of Radix Ophiopogonis, and less than 5 wt % of Radix Puerariae, 10 wt % of Flos Carthami, 5-10 wt % of Semen Dolichoris, 5-10 wt % of Lophatherum gracile Brongn, 5 wt % of Herba Gynostemmatis, 3-5 wt % of Porphyra tenera, 1 wt % of Semen Euryales, 5-10 wt % of Psidium guajava leaf, 5-10 wt % of Avena sativa, and 2-25 wt % of bamboo cellulose.

The herbal compositions are mostly used in the form of powder mixture. However, the herbal compositions may also be made into capsule, sachet, suspension or tablet with pharmaceutically acceptable carriers. The herbal compositions are preferred to be formulated to be administered orally, but formulated for parenteral administrations is also acceptable.

Some embodiments of the present invention provide methods of regulating blood glucose levels with the herbal compositions. The methods comprise a step of administering a therapeutically effective amount of the herbal composition to a subject for a period of time, in which the step of administering is applied before a meal. In some certain embodiments, the step of administering is applied 10-30 minutes before a meal; in yet some certain embodiments, the step of administering is applied 30 minutes before a meal. In some certain embodiments, the period of time is at least 1 mouth; in yet some certain embodiments, the period of time is at least 3 mouths. In some certain embodiments, the therapeutically effective amount is ranging from 6 to 20 g; in yet some certain embodiments, the therapeutically effective amount is ranging from 8 to 16 g.

The herbal compositions in some embodiments of the present invention are used as supplements to tonify carbohydrate metabolism in the body. In some other embodiments, the herbal compositions are used with other medical therapies or drugs, regulating glycemic levels, as adjuvants. In still some other embodiments, the herbal compositions are further formulated and used as medicines for treatment of subjects with poor glycemic control. The herbal compositions effectively improve the homeostasis of blood glucose levels in the body and may be used for subjects with some medical conditions, such as hyperglycemia, Diabetes mellitus, and obesity.

It will be appreciated that the dosage of compounds of the herbal compositions will vary from subject to subject not only for the particular compound or composition selected, the route of administration, and the ability of the compound (alone or in combination with one or more drugs) to elicit a desired response in the subject, but also factors such as physical state or severity of the condition to be alleviated, age, sex, weight of the subject, and other factors which those skilled in the art will recognize, with the appropriate dosage ultimately being at the discretion of the attendant physician.

The following exemplary embodiments will now be described more specifically, which are provided for the purpose of demonstration rather than limitation.

The first exemplary embodiment provided an herbal composition to a subject, with high glucose AC and HbAlC values, for about 4 months. The herbal composition comprises 10 wt % of Radix Dioscoreae, 10 wt % Radix Codonopsis, and 10 wt % of Radix Astragalus Membranaceus, in which each herbal component were made in powdered form. And 8 g of the herbal composition was administered orally half an hour before each meal. The results were shown in Table I.

TABLE I

|  | Day 0 | Day 40 | Day 126 |
| --- | --- | --- | --- |
| Glucose AC (mg/dl) | 151 | 138 | 107 |
| HbAlC (%) | 8.1 | 7.5 | 7.3 |
| GOT (U/L) | 25 | 24 | 18 |
| GPT (U/L) | 41 | 36 | 27 |

The second exemplary embodiment provided an herbal composition to a subject, with high glucose AC and HbAlC values, for about 3 months. The herbal composition comprises 10 wt % of Radix Dioscoreae, 10 wt % Radix Codonopsis, 10 wt % of Radix Astragalus Membranaceus, 3 wt % of Herba Dendrobii, 10 wt % of Radix Ophiopogonis, and less than 5 wt % of Radix Puerariae, 10 wt % of Flos Carthami, 5 wt % of Semen Dolichoris, 5 wt % of Lophatherum gracile Brongn, 5 wt % of Herba Gynostemmatis, 5 wt % of Porphyra tenera, 1 wt % of Semen Euryales, 5 wt % of Psidium guajava leaf, 5 wt % of Avena sativa, and 10 wt % of bamboo cellulose, in which each herbal component were made in powdered form. And 8 g of the herbal composition was administered orally half an hour before each meal. The results were shown in Table II.

TABLE II

|  | Day 0 | Day 83 |
| --- | --- | --- |
| Glucose AC (mg/dl) | 172 | 92 |
| HbAlC (%) | 8.2 | 7.4 |
| GOT (U/L) | 60 | 55 |
| GPT (U/L) | 87 | 67 |

The exemplary embodiments show that the herbal compositions had effectively improved the quality of glycemic control in the body. Values including glucose AC, HbAlC, GOT, and GPT were steadily reduced after treated with the herbal compositions.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A herbal composition for glycemic control, comprising 10 wt % of Radix Dioscoreae, 10 wt % of Radix Codonopsis, 10 wt % of Radix Astragalus Membranaceus, 3 wt % of Herba Dendrobii, 10 wt % of Radix Ophiopogonis, less than 5 wt % of Radix Puerariae, 10 wt % of Flos Carthami, 5-10 wt % of Semen Dolichoris, 5-10 wt % of Lophatherum gracile Brongn, 5 wt % of Herba Gynostemmatis, 3-5 wt % of Porphyra tenera, 1 wt % of Semen Euryales, 5-10 wt % of Psidium guajava leaf, 5-10 wt % of Avena sativa, and 2-25 wt % of bamboo cellulose.

2. The herbal composition according to claim 1, wherein the herbal composition further comprises a pharmaceutically acceptable carrier.

3. The herbal composition according to claim 1, wherein the herbal composition is formulated to be administered orally.

4. The herbal composition according to claim 3, wherein the herbal composition suppresses intestinal glucose uptake of intestinal villus.

5. A method of regulating blood glucose levels, comprising:
    administering a therapeutically effective amount of the herbal composition according to claim 1 to a subject in need thereof for a period of time;
    wherein the administering step is applied before a meal.

6. The method according to claim 5, wherein the administering step is applied 10-30 minutes before the meal.

7. The method according to claim 5, wherein the therapeutically effective amount ranges from 6 to 20 g.

* * * * *